US009629975B1

(12) United States Patent
Pedro et al.

(10) Patent No.: US 9,629,975 B1
(45) Date of Patent: Apr. 25, 2017

(54) VENTILATION MASK

(71) Applicant: Revolutionary Medical Devices, INC., Tucson, AZ (US)

(72) Inventors: Michael J. Pedro, Brooklyn, NY (US); David M. Kane, Tucson, AZ (US); Ryan Redford, Tucson, AZ (US)

(73) Assignee: REVOLUTIONARY MEDICAL DEVICES, INC., Tucson, AZ (US)

( * ) Notice: Subject to any disclaimer, the term of this patent is extended or adjusted under 35 U.S.C. 154(b) by 0 days.

(21) Appl. No.: 15/288,973

(22) Filed: Oct. 7, 2016

Related U.S. Application Data

(60) Provisional application No. 62/394,405, filed on Sep. 14, 2016.

(51) Int. Cl.
| A61M 16/06 | (2006.01) |
| A61M 16/08 | (2006.01) |
| A61M 16/01 | (2006.01) |
| A61M 16/00 | (2006.01) |

(52) U.S. Cl.
CPC .... *A61M 16/0683* (2013.01); *A61M 16/0078* (2013.01); *A61M 16/01* (2013.01); *A61M 16/06* (2013.01); *A61M 16/085* (2014.02); *A61M 2202/0208* (2013.01); *A61M 2230/432* (2013.01)

(58) Field of Classification Search
CPC .. A61M 16/01; A61M 16/06; A61M 16/0666; A61M 16/0672; A61M 16/0677; A61M 16/085; A61M 16/104; A61M 2016/103
See application file for complete search history.

(56) References Cited

U.S. PATENT DOCUMENTS

| 1,050,621 | A | * | 1/1913 | Ford | A61M 16/06 |
| | | | | | 128/206.28 |
| 1,131,802 | A | | 3/1915 | Stenshoel | |
| 1,441,817 | A | | 1/1923 | McCullough | |
| 1,729,525 | A | | 9/1929 | Stenshoel | |
| 1,776,167 | A | | 9/1930 | Stenshoel | |
| 2,452,816 | A | | 11/1948 | Wagner | 311/10 |
| 3,013,556 | A | | 12/1961 | Galleher | |
| 3,522,612 | A | | 8/1970 | Palmer | 2/88 |
| 3,556,097 | A | | 1/1971 | Wallace | 128/188 |
| 3,815,596 | A | | 6/1974 | Keener et al. | 128/188 |

(Continued)

FOREIGN PATENT DOCUMENTS

| CN | 202478364 | 10/2012 | ............ A61M 16/06 |
| DE | 19947722 | 4/2001 | ............ A61M 16/06 |

(Continued)

OTHER PUBLICATIONS

International Search Report and Written Opinion issued in application No. PCT/US2016/037070, dated Nov. 10, 2016 (11 pgs).

(Continued)

*Primary Examiner* — Valerie L Woodward
(74) *Attorney, Agent, or Firm* — Hayes Soloway P.C.

(57) ABSTRACT

A method for ventilating a patient in which nasal mask having an exhalation scoop formed of a flexible or resiliently deformable material, fixed adjacent a lower portion of mask, is positioned to overlie an upper lip of a patient. When needed, the exhalation scoop is folded back on itself to provide access to the patient's mouth.

7 Claims, 4 Drawing Sheets

(56) References Cited

U.S. PATENT DOCUMENTS

| | | | |
|---|---|---|---|
| 3,856,051 A | 12/1974 | Bain | 138/114 |
| 3,889,668 A | 6/1975 | Ochs et al. | 128/134 |
| 3,897,777 A | 8/1975 | Morrison | 128/133 |
| D242,490 S | 11/1976 | Belkin | D83/1 R |
| 4,005,499 A | 2/1977 | Klein | 5/485 |
| 4,007,737 A | 2/1977 | Paluch | 128/188 |
| 4,188,946 A | 2/1980 | Watson et al. | 128/204.22 |
| D256,161 S | 7/1980 | Oliver | D6/602 |
| 4,231,363 A * | 11/1980 | Grimes | A61M 16/06 |
| | | | 128/205.25 |
| 4,232,667 A | 11/1980 | Chalon et al. | 128/203.26 |
| 4,248,218 A | 2/1981 | Fischer | 128/204.18 |
| 4,259,757 A | 4/1981 | Watson | 5/434 |
| 4,265,235 A | 5/1981 | Fukunaga | 128/200.24 |
| 4,275,720 A | 6/1981 | Wichman | 128/853 |
| 4,328,797 A | 5/1982 | Rollins | 128/202.15 |
| 4,457,026 A | 7/1984 | Morris | 2/171 |
| 4,463,755 A | 8/1984 | Suzuki | 128/204.18 |
| 4,471,769 A | 9/1984 | Lockhart | 128/849 |
| 4,574,796 A | 3/1986 | Lundstrom | 128/855 |
| 4,596,246 A | 6/1986 | Lyall | 128/202.27 |
| 4,657,010 A * | 4/1987 | Wright | A61M 16/06 |
| | | | 128/205.25 |
| 4,700,691 A | 10/1987 | Tari et al. | 128/1 R |
| 4,905,712 A | 3/1990 | Bowlin et al. | 128/870 |
| 5,046,200 A | 9/1991 | Feder | 2/452 |
| 5,121,746 A | 6/1992 | Sikora | 128/203.12 |
| D333,404 S | 2/1993 | Thompson | D6/602 |
| 5,243,971 A | 9/1993 | Sullivan et al. | 128/205.25 |
| 5,255,303 A | 10/1993 | DiMaio et al. | 378/177 |
| 5,271,390 A | 12/1993 | Gray et al. | 128/207.12 |
| 5,284,160 A | 2/1994 | Dryden | 128/203.12 |
| D347,494 S | 5/1994 | Mustelier | D24/110.4 |
| D354,128 S | 1/1995 | Rinehart | D24/110.1 |
| 5,404,873 A | 4/1995 | Leagre et al. | 128/204.18 |
| 5,462,050 A | 10/1995 | Dahlstrand | 128/207.18 |
| 5,474,060 A | 12/1995 | Evans | 128/204.22 |
| 5,485,837 A | 1/1996 | Solesbee et al. | 128/207.17 |
| 5,524,639 A | 6/1996 | Lanier et al. | 128/845 |
| D373,921 S | 9/1996 | Palomo et al. | D6/602 |
| RE35,339 E | 10/1996 | Rapoport | 128/204.18 |
| 5,560,354 A | 10/1996 | Berthon-Jones et al. | 128/205.25 |
| 5,586,551 A | 12/1996 | Hilliard | 128/200.14 |
| 5,647,357 A | 7/1997 | Barnett et al. | 128/206.24 |
| 5,649,331 A | 7/1997 | Wilkinson et al. | 5/710 |
| 5,660,174 A | 8/1997 | Jacobelli | 128/206.24 |
| 5,661,859 A | 9/1997 | Schaefer | 5/621 |
| 5,685,298 A | 11/1997 | Idris | 128/206.12 |
| 5,738,094 A | 4/1998 | Hoftman | 128/206.26 |
| 5,746,201 A | 5/1998 | Kidd | 128/206.24 |
| 5,749,358 A | 5/1998 | Good et al. | 128/205.23 |
| 5,778,872 A | 7/1998 | Fukunaga et al. | 128/202.27 |
| D402,755 S | 12/1998 | Kwok | D24/110 |
| 5,884,624 A | 3/1999 | Barnett et al. | 128/206.24 |
| 5,933,886 A | 8/1999 | Washington | 5/494 |
| 5,966,763 A | 10/1999 | Thomas et al. | 5/715 |
| 5,975,079 A | 11/1999 | Hellings et al. | 128/206.24 |
| 5,983,896 A | 11/1999 | Fukunaga et al. | 128/207.14 |
| 6,003,511 A | 12/1999 | Fukunaga et al. | 128/202.27 |
| 6,019,101 A | 2/2000 | Cotner et al. | 128/207.13 |
| 6,035,852 A | 3/2000 | Hoftman | 128/206.26 |
| 6,058,933 A | 5/2000 | Good et al. | 128/205.13 |
| D428,987 S | 8/2000 | Kwok | D24/110.1 |
| 6,112,746 A | 9/2000 | Kwok et al. | 128/207.13 |
| 6,123,071 A | 9/2000 | Berthon-Jones et al. | 128/204.18 |
| 6,129,082 A | 10/2000 | Leagre | 128/205.29 |
| 6,152,137 A | 11/2000 | Schwartz et al. | 128/846 |
| D435,650 S | 12/2000 | Kwok | D24/110.1 |
| 6,192,886 B1 | 2/2001 | Rudolph | 128/207.13 |
| 6,216,691 B1 | 4/2001 | Kenyon et al. | 128/205.18 |
| 6,263,874 B1 * | 7/2001 | LeDez | A61M 16/009 |
| | | | 128/205.25 |
| 6,357,441 B1 | 3/2002 | Kwok et al. | 128/207.13 |
| 6,397,847 B1 | 6/2002 | Scarberry et al. | 128/206.24 |
| 6,412,487 B1 | 7/2002 | Gunaratnam et al. | 128/206.24 |
| 6,412,488 B1 | 7/2002 | Barnett et al. | 128/207.13 |
| 6,439,230 B1 | 8/2002 | Gunaratnam et al. | 128/206.21 |
| 6,439,231 B1 | 8/2002 | Fukunaga et al. | 128/207.14 |
| 6,446,288 B1 | 9/2002 | Pi | 5/636 |
| 6,459,923 B1 | 10/2002 | Plewes et al. | 600/411 |
| 6,463,931 B1 | 10/2002 | Kwok et al. | 128/207.11 |
| 6,467,483 B1 | 10/2002 | Kopacko et al. | 128/207.12 |
| D467,345 S | 12/2002 | Gingles et al. | D24/189 |
| 6,513,526 B2 | 2/2003 | Kwok et al. | 128/206.24 |
| 6,520,182 B1 | 2/2003 | Gunaratnam | 128/206.27 |
| 6,581,602 B2 | 6/2003 | Kwok et al. | 128/207.13 |
| 6,612,306 B1 | 9/2003 | Mault | 128/204.22 |
| 6,626,178 B2 | 9/2003 | Morgan et al. | 128/206.26 |
| 6,631,718 B1 | 10/2003 | Lovell | 128/206.24 |
| 6,634,358 B2 | 10/2003 | Kwok et al. | 128/205.25 |
| 6,651,663 B2 | 11/2003 | Barnett et al. | 128/207.13 |
| 6,694,973 B1 | 2/2004 | Dunhao et al. | 128/203.12 |
| 6,701,927 B2 | 3/2004 | Kwok et al. | 128/207.13 |
| 6,729,333 B2 | 5/2004 | Barnett et al. | 128/207.13 |
| 6,736,139 B1 | 5/2004 | Wix | 128/206.21 |
| D493,523 S | 7/2004 | Barnett et al. | D24/110.4 |
| 6,779,524 B2 | 8/2004 | Strawder et al. | 128/206.21 |
| 6,792,943 B2 | 9/2004 | Kumar et al. | 128/200.26 |
| 6,796,308 B2 | 9/2004 | Gunaratnam et al. | 128/206.24 |
| 6,805,117 B1 | 10/2004 | Ho et al. | 128/201.22 |
| 6,832,610 B2 | 12/2004 | Gradon et al. | 128/206.27 |
| 6,863,071 B2 | 3/2005 | Annett et al. | 128/849 |
| 6,871,649 B2 | 3/2005 | Kwok et al. | 128/206.24 |
| 6,892,729 B2 | 5/2005 | Smith et al. | 128/204.18 |
| 6,895,965 B2 | 5/2005 | Scarberry et al. | 128/206.24 |
| 6,931,664 B2 | 8/2005 | Chen | 2/9 |
| 6,935,337 B2 | 8/2005 | Virr et al. | 128/203.16 |
| 6,981,503 B1 | 1/2006 | Shapiro | 128/845 |
| 7,004,168 B2 | 2/2006 | Mace et al. | 128/206.21 |
| 7,007,696 B2 | 3/2006 | Palkon et al. | 128/207.13 |
| 7,013,896 B2 | 3/2006 | Schmidt | 128/206.15 |
| 7,017,576 B2 | 3/2006 | Olsen et al. | 128/205.25 |
| 7,021,311 B2 | 4/2006 | Gunaratnam et al. | 128/206.24 |
| 7,036,508 B2 | 5/2006 | Kwok | 128/207.11 |
| 7,047,971 B2 | 5/2006 | Ho et al. | 128/207.11 |
| 7,066,179 B2 | 6/2006 | Eaton et al. | 128/206.27 |
| 7,069,932 B2 | 7/2006 | Eaton et al. | 128/206.24 |
| 7,069,933 B2 | 7/2006 | Kwok et al. | 128/206.24 |
| 7,114,498 B1 | 10/2006 | Nashed | 128/205.27 |
| 7,159,587 B2 | 1/2007 | Drew et al. | 128/204.18 |
| 7,178,524 B2 | 2/2007 | Noble | 128/206.11 |
| 7,178,527 B2 | 2/2007 | Kwok et al. | 128/207.13 |
| 7,210,481 B1 | 5/2007 | Lovell et al. | 128/205.25 |
| 7,219,669 B1 | 5/2007 | Lovell et al. | 128/206.24 |
| 7,237,551 B2 | 7/2007 | Ho et al. | 128/207.13 |
| 7,243,651 B2 | 7/2007 | Kwok et al. | 128/205.25 |
| 7,287,528 B2 | 10/2007 | Ho et al. | 128/206.21 |
| 7,341,060 B2 | 3/2008 | Ging et al. | 128/206.11 |
| 7,383,839 B2 | 6/2008 | Porat et al. | 128/207.18 |
| 7,445,602 B2 * | 11/2008 | Yamamori | A61B 5/0836 |
| | | | 128/201.27 |
| 7,448,386 B2 | 11/2008 | Ho et al. | 128/206.21 |
| 7,467,431 B2 | 12/2008 | Weedling et al. | 5/633 |
| 7,487,772 B2 | 2/2009 | Ging et al. | 128/202.27 |
| 7,487,777 B2 | 2/2009 | Gunaratnam et al. | 128/206.24 |
| 7,500,280 B2 | 3/2009 | Dixon et al. | 5/713 |
| 7,500,482 B2 | 3/2009 | Biederman | 128/206.21 |
| 7,614,398 B2 | 11/2009 | Virr et al. | 128/203.26 |
| 7,631,644 B2 | 12/2009 | Ho et al. | 128/206.21 |
| 7,665,464 B2 | 2/2010 | Kopacko et al. | 128/206.24 |
| 7,669,599 B2 | 3/2010 | Gunaratnam et al. | 128/205.25 |
| 7,700,129 B2 | 4/2010 | Ito et al. | 424/486 |
| 7,743,767 B2 | 6/2010 | Ging et al. | 128/206.24 |
| 7,753,051 B2 | 7/2010 | Burrow et al. | 128/207.11 |
| 7,779,832 B1 | 8/2010 | Ho | 128/201.22 |
| 7,841,988 B2 | 11/2010 | Yamamori | 600/532 |
| 7,870,859 B2 | 1/2011 | Barnett et al. | 128/204.24 |
| 7,874,292 B2 | 1/2011 | Smith et al. | 128/206.27 |
| 7,913,337 B1 | 3/2011 | Masson | 5/618 |
| 7,926,487 B2 | 4/2011 | Drew et al. | 128/205.25 |
| 7,927,285 B2 | 4/2011 | Yamamori | 600/532 |

(56) References Cited

U.S. PATENT DOCUMENTS

| | | | |
|---|---|---|---|
| 7,931,024 B2 | 4/2011 | Ho et al. | 128/206.21 |
| 7,938,117 B2 | 5/2011 | Chiesa et al. | 128/205.25 |
| 7,950,392 B2 | 5/2011 | Kwok et al. | 128/206.24 |
| 7,975,694 B2 | 7/2011 | Ho | 128/207.13 |
| 7,997,267 B2 | 8/2011 | Ging et al. | 128/202.27 |
| 8,001,968 B2 | 8/2011 | Doty et al. | 128/205.27 |
| 8,001,970 B2 | 8/2011 | King et al. | 128/845 |
| 8,028,699 B2 | 10/2011 | Ho et al. | 128/206.21 |
| 8,042,539 B2 | 10/2011 | Chandran et al. | 128/206.28 |
| 8,042,541 B2 | 10/2011 | Amarasinghe et al. | 128/206.27 |
| 8,056,561 B2 | 11/2011 | Kwok et al. | 128/206.24 |
| 8,132,270 B2 | 3/2012 | Lang et al. | 2/422 |
| 8,161,971 B2 * | 4/2012 | Jaffe | A61M 16/0666 128/200.24 |
| 8,191,553 B2 | 6/2012 | Haworth et al. | 128/845 |
| 8,210,181 B2 | 7/2012 | Gunaratnam et al. | 128/207.11 |
| 8,261,745 B2 | 9/2012 | Chandran et al. | 128/206.24 |
| 8,261,746 B2 | 9/2012 | Lynch et al. | 128/206.24 |
| 8,267,091 B2 | 9/2012 | Smith et al. | 128/202.27 |
| 8,302,224 B2 | 11/2012 | Lehmann | 5/486 |
| 8,312,883 B2 | 11/2012 | Gunaratnam et al. | 128/207.18 |
| 8,336,142 B1 | 12/2012 | See et al. | 5/634 |
| 8,336,549 B2 | 12/2012 | Nashed | 128/206.28 |
| 8,347,889 B2 | 1/2013 | Farnum | 128/845 |
| 8,365,734 B1 | 2/2013 | Lehman | 128/206.28 |
| 8,397,724 B2 | 3/2013 | Sher et al. | 128/205.25 |
| D681,383 S | 5/2013 | Derman et al. | D6/603 |
| 8,443,807 B2 | 5/2013 | McAuley et al. | 128/207.18 |
| 8,479,726 B2 | 7/2013 | McAuley | 128/201.17 |
| 8,485,190 B2 | 7/2013 | Barnett et al. | 128/206.24 |
| 8,485,192 B2 | 7/2013 | Davidson et al. | 128/206.24 |
| 8,490,623 B2 | 7/2013 | Berthon-Jones et al. | 128/206.21 |
| RE44,453 E | 8/2013 | Virr et al. | 128/203.27 |
| 8,522,783 B2 | 9/2013 | Kwok et al. | 128/204.26 |
| 8,528,558 B2 | 9/2013 | Drew et al. | 128/205.25 |
| 8,550,081 B2 | 10/2013 | Davidson et al. | 128/206.24 |
| 8,550,082 B2 | 10/2013 | Davidson et al. | 128/206.24 |
| 8,550,083 B2 | 10/2013 | Davidson et al. | 128/206.24 |
| 8,555,885 B2 | 10/2013 | Davidson et al. | 128/206.24 |
| 8,567,402 B2 | 10/2013 | Gunaratnam et al. | 128/205.25 |
| 8,567,404 B2 | 10/2013 | Davidson et al. | 128/206.24 |
| D693,603 S | 11/2013 | Esquivel et al. | D6/602 |
| 8,573,211 B2 | 11/2013 | Ho et al. | 128/206.24 |
| 8,573,212 B2 | 11/2013 | Lynch et al. | 128/206.24 |
| 8,573,213 B2 | 11/2013 | Davidson et al. | 128/206.24 |
| 8,573,214 B2 | 11/2013 | Davidson et al. | 128/206.24 |
| 8,573,215 B2 | 11/2013 | Davidson et al. | 128/206.24 |
| 8,573,217 B2 | 11/2013 | Todd et al. | 128/207.12 |
| 8,578,935 B2 | 11/2013 | Davidson et al. | 128/206.24 |
| 8,578,939 B1 | 11/2013 | Kimani Mwangi et al. | 128/848 |
| 8,613,280 B2 | 12/2013 | Davidson et al. | 128/206.24 |
| 8,613,281 B2 | 12/2013 | Davidson et al. | 128/206.24 |
| 8,616,211 B2 | 12/2013 | Davidson et al. | 128/206.24 |
| 8,631,792 B2 | 1/2014 | Ho et al. | 128/206.24 |
| 8,636,006 B2 | 1/2014 | Kwok et al. | 128/207.13 |
| 8,667,965 B2 | 3/2014 | Gunaratnam et al. | 128/207.13 |
| 8,684,004 B2 | 4/2014 | Eifler | 128/206.24 |
| 8,689,366 B2 | 4/2014 | Ho | 2/452 |
| 8,714,157 B2 | 5/2014 | McAuley et al. | 128/205.25 |
| 8,752,551 B2 | 6/2014 | Chandran et al. | 128/206.28 |
| 8,807,134 B2 | 8/2014 | Ho et al. | 128/206.21 |
| 8,807,135 B2 | 8/2014 | Worboys et al. | 128/206.24 |
| 8,813,748 B2 | 8/2014 | Kwok et al. | 128/206.24 |
| 8,881,728 B2 | 11/2014 | Sher et al. | 128/205.25 |
| 8,915,861 B2 | 12/2014 | Yamamori et al. | 600/532 |
| 8,939,151 B2 | 1/2015 | McAuley et al. | 128/205.25 |
| 8,944,061 B2 | 2/2015 | D'Souza et al. | 128/206.24 |
| D726,303 S | 4/2015 | Rollins | D24/110.1 |
| 9,010,330 B2 | 4/2015 | Barlow et al. | 128/201.18 |
| 9,010,331 B2 | 4/2015 | Lang et al. | A61M 16/06 |
| 9,022,029 B2 | 5/2015 | Varga et al. | A61B 5/0836 |
| 9,027,556 B2 | 5/2015 | Ng et al. | 128/205.25 |
| 9,138,169 B2 | 9/2015 | Beard | A61B 5/097 |
| 9,186,474 B1 | 11/2015 | Rollins | |
| 9,295,799 B2 | 3/2016 | McAuley et al. | A61M 16/06 |
| 9,295,800 B2 | 3/2016 | Davidson et al. | A61M 16/06 |
| D753,287 S | 4/2016 | Darab | D24/110.4 |
| D753,816 S | 4/2016 | Beard | D24/110.4 |
| 9,375,545 B2 | 6/2016 | Darkin et al. | A61M 16/0683 |
| 2002/0074001 A1 | 6/2002 | Kwok et al. | |
| 2003/0024533 A1 | 2/2003 | Sniadach | 128/205.25 |
| 2003/0183232 A1 | 10/2003 | Fukunaga et al. | 128/204.18 |
| 2004/0069306 A1 | 4/2004 | Moenning | 128/207.13 |
| 2005/0160532 A1 | 7/2005 | Froelich | 5/637 |
| 2005/0193493 A1 | 9/2005 | Gabbay | 5/644 |
| 2006/0032500 A1 | 2/2006 | Ghiron et al. | 128/202.27 |
| 2006/0042631 A1 | 3/2006 | Martin et al. | 128/207.18 |
| 2006/0124131 A1 | 6/2006 | Chandran et al. | |
| 2006/0168730 A1 | 8/2006 | Menkedick et al. | 5/618 |
| 2006/0231091 A1 | 10/2006 | Camarillo | 128/200.21 |
| 2007/0113856 A1 | 5/2007 | Acker et al. | 128/207.14 |
| 2007/0271699 A1 | 11/2007 | Sacchetti | 5/495 |
| 2007/0295335 A1 | 12/2007 | Nashed | 128/206.24 |
| 2008/0092898 A1 | 4/2008 | Schneider et al. | 128/206.28 |
| 2008/0221470 A1 | 9/2008 | Sather et al. | 600/533 |
| 2008/0230067 A1 | 9/2008 | Kwok et al. | 128/206.24 |
| 2009/0114229 A1 | 5/2009 | Frater et al. | 128/206.24 |
| 2009/0133696 A1 | 5/2009 | Remmers et al. | 128/204.26 |
| 2009/0178680 A1 | 7/2009 | Chang | 128/206.27 |
| 2009/0250061 A1 | 10/2009 | Marasigan | 128/205.13 |
| 2009/0260628 A1 | 10/2009 | Flynn | 128/203.28 |
| 2009/0320850 A1 | 12/2009 | Wallnewitz et al. | 128/207.11 |
| 2010/0122701 A1 | 5/2010 | Gunaratnam | |
| 2010/0147313 A1 | 6/2010 | Albrecht | 128/845 |
| 2010/0170513 A1 | 7/2010 | Bowditch | 128/204.23 |
| 2010/0170516 A1 | 7/2010 | Grane | |
| 2010/0218316 A1 | 9/2010 | Nissen et al. | 5/632 |
| 2010/0224199 A1 | 9/2010 | Smith et al. | 128/863 |
| 2010/0275919 A1 | 11/2010 | Sung | 128/204.22 |
| 2010/0313891 A1 | 12/2010 | Veliss et al. | |
| 2011/0054366 A1 | 3/2011 | Smith et al. | 601/15 |
| 2011/0072582 A1 | 3/2011 | Patterson et al. | 5/484 |
| 2011/0083670 A1 | 4/2011 | Walacavage | 128/205.12 |
| 2011/0092930 A1 | 4/2011 | Poorman | 604/356 |
| 2011/0108035 A1 * | 5/2011 | Samaniego | A62B 18/025 128/206.17 |
| 2011/0155136 A1 | 6/2011 | Lee | 128/205.24 |
| 2011/0173750 A1 | 7/2011 | Lehmann | 5/486 |
| 2011/0186050 A1 | 8/2011 | Daly | 128/204.23 |
| 2011/0214674 A1 | 9/2011 | Ging et al. | 128/206.21 |
| 2011/0253150 A1 | 10/2011 | King | 128/845 |
| 2011/0265796 A1 | 11/2011 | Amarasinghe et al. | 128/206.28 |
| 2012/0080035 A1 | 4/2012 | Guney et al. | 128/205.25 |
| 2012/0111330 A1 | 5/2012 | Gartner | 128/205.23 |
| 2012/0144588 A1 | 6/2012 | Heimbrock et al. | 5/624 |
| 2012/0180220 A1 | 7/2012 | Popitz | 5/638 |
| 2012/0227736 A1 | 9/2012 | Bowsher | 128/202.27 |
| 2012/0247475 A1 | 10/2012 | Hernandez et al. | |
| 2012/0285455 A1 | 11/2012 | Varga et al. | 128/204.21 |
| 2013/0014760 A1 | 1/2013 | Matula, Jr. et al. | 128/205.25 |
| 2013/0023729 A1 | 1/2013 | Vazales | |
| 2013/0060157 A1 * | 3/2013 | Beard | A61M 16/06 600/532 |
| 2013/0146060 A1 | 6/2013 | Ho et al. | 128/205.25 |
| 2013/0186413 A1 | 7/2013 | Haines et al. | 128/854 |
| 2013/0190643 A1 | 7/2013 | Brambilla | A61M 16/0875 |
| 2013/0192601 A1 | 8/2013 | Reischl et al. | 128/205.25 |
| 2013/0192602 A1 | 8/2013 | Leibitzki et al. | 128/205.27 |
| 2013/0199537 A1 | 8/2013 | Formica et al. | A61M 16/0666 |
| 2013/0319417 A1 | 12/2013 | Weinman | 128/205.25 |
| 2014/0076311 A1 | 3/2014 | Darab | 128/203.12 |
| 2014/0083425 A1 | 3/2014 | Moenning | 128/203.29 |
| 2014/0144448 A1 | 5/2014 | Eifler | 128/206.24 |
| 2014/0158135 A1 | 6/2014 | Shyong | 128/206.21 |
| 2014/0158136 A1 | 6/2014 | Romagnoli et al. | 128/206.24 |
| 2014/0215687 A1 | 8/2014 | Andrews | 2/170 |
| 2014/0243600 A1 | 8/2014 | Eisenberger | 600/410 |
| 2014/0245537 A1 | 9/2014 | Allen | 5/622 |
| 2014/0251333 A1 | 9/2014 | Burk | 128/205.12 |
| 2014/0326246 A1 | 11/2014 | Chodkowski et al. | 128/206.24 |
| 2014/0352072 A1 | 12/2014 | Holladay | 5/655.5 |
| 2014/0360504 A1 | 12/2014 | Kwok | A61M 16/0605 |
| 2015/0047647 A1 | 2/2015 | Winer | 128/854 |

(56) References Cited

U.S. PATENT DOCUMENTS

| | | | |
|---|---|---|---|
| 2015/0059759 A1 | 3/2015 | Frater et al. | 128/205.25 |
| 2015/0144140 A1 | 5/2015 | Eury | A61M 16/0622 |
| 2015/0217075 A1 | 8/2015 | Nair | 600/531 |
| 2015/0238716 A1 | 8/2015 | Budhiraja et al. | A61M 16/0003 |
| 2015/0250970 A1 | 9/2015 | Bowsher | 16/616 |
| 2015/0250971 A1 | 9/2015 | Bachelder et al. | A61M 16/0616 |
| 2015/0273170 A1 | 10/2015 | Bachelder et al. | A61M 16/0616 |
| 2015/0273171 A1 | 10/2015 | Sullivan et al. | A61M 16/0683 |
| 2015/0335852 A1 | 11/2015 | Miller | A61M 16/208 |
| 2016/0015923 A1 | 1/2016 | Chodkowski et al. | A61M 16/0622 |
| 2016/0022944 A1 | 1/2016 | Chodkowski et al. | A61M 16/0616 |
| 2016/0038709 A1 | 2/2016 | Beard | 128/205.12 |
| 2016/0067441 A1 | 3/2016 | Bearne et al. | A61M 16/0683 |
| 2016/0184540 A1 | 6/2016 | Kokko | A61M 16/0069 |
| 2016/0213871 A1 | 7/2016 | Darab | |

FOREIGN PATENT DOCUMENTS

| | | | |
|---|---|---|---|
| EP | 2433666 | 3/2012 | A61M 16/06 |
| GB | 2456136 | 7/2009 | |
| WO | WO2010059592 | 5/2010 | A61M 16/06 |
| WO | WO2013036839 | 3/2013 | A61M 16/06 |
| WO | WO2014038959 | 3/2014 | A61M 16/00 |
| WO | WO2014210606 | 12/2014 | A61G 13/02 |
| WO | WO2015063283 | 5/2015 | A61M 16/06 |
| WO | WO2015131262 | 9/2015 | A61M 16/06 |
| WO | WO2015147947 | 10/2015 | A61M 15/06 |
| WO | WO2016007749 | 1/2016 | A61M 16/10 |
| WO | WO2016097948 | 6/2016 | A61M 16/06 |

OTHER PUBLICATIONS

Japanese Office Action (w/translation) issued in application No. 2016-006559, dated Aug. 29, 2016 (3 pgs).
Japanese Office Action (w/translation) issued in application No. 2016-006560, dated Aug. 29, 2016 (3 pgs).
Australian Certificate of Registration issued in application No. 201512961, dated Aug. 10, 2015 (5 pgs).
Australian Certificate of Registration issued in application No. 201512962, dated Aug. 12, 2015 (5 pgs).
Ball et al., "Performance comparison of two anaesthetic facemasks," Anaesth Intensive Care, Apr. 2007, vol. 35, issue 2, 226-9 (abstract only) (2 pgs).
Canadian Office Action issued in application No. 162891, dated Apr. 5, 2016 (1 pg).
Canadian Office Action issued in application No. 162891, dated Nov. 10, 2015 (7 pgs).
CPAP product description, http://www.cpap.com/productpage/pr-amara-full-face-cpap-mask-gel-silicone.html, downloaded Jul. 28, 2016, 11 pages.
CPAPXCHANGE product image, http://www.cpapxchange.com/cpap-masks-bipap-masks/bluegel-full-cushion-comfortgel-cpap-bipap-masks.jpg, downloaded Jul. 28, 2016, 1 page.
DirectHome Medical product description, http://www.directhomemedical.com/profilelite-gel-cpap-mask-philipsrespironics.html#.VwXLIPkrLIU, downloaded Jul. 28, 2016, 6 pages.
Indian Office Action issued in related Indian Design Patent Application Serial No. 272704, dated Aug. 28. 2015 (13 pgs).
InnoMed Technologies Hybrid mask product description, http://innomedinc.com/hybrid/, downloaded Jul. 28, 2016,4 pages.
InnoMed Technologies Sylent mask product description, http://innomedinc.com/svlent-ne-disposable-nasal-mask/, downloaded Jul. 28, 2016, 2 pages.
International Preliminary Report on Patentability issued in application No. PCT/US14/44934, dated Jan. 7, 2016 (12 pgs).
International Preliminary Report on Patentability issued in application No. PCT/US2105/021323, dated Oct. 6, 2016 (8 pgs).
International Search Report and Written Opinion issued in application No. PCT/US2015/044341, dated Jan. 7, 2016 (13 pgs).
International Search Report and Written Opinion issued in application No. PCT/US2015/34277, dated Nov. 23, 2015 (16 pgs).
International Search Report issued in application No. PCT/US14/44934, dated Jan. 2, 2015 (16 pgs).
Invitation to Pay Additional Fees issued in application No. PCT/US15/44341, dated Oct. 21, 2015 (2 pgs).
Invitation to Pay Additional Fees issued in application No. PCT/US14/44934, dated Oct. 24, 2014 (3 pgs).
Israeli Notice of Allowance issued in application No. 57056 (no translation), dated May 29, 2016 (1 pg).
Israeli Office Action issued in application No. 57056 (w/translation of relevant portions), dated Nov. 1, 2015 (3 pgs).
Israeli Office Action issued in application No. 57850 (w/translation of relevant portions), dated Feb. 15, 2016 (3 pgs).
Israeli Office Action issued in application No. 57850 (w/translation of relevant portions), dated Jun. 30, 2016 (2 pgs).
Israeli Office Action issued in application No. 57850 (w/translation of relevant portions), dated Jul. 19, 2016 (3 pgs).
Japanese Office Action issued in application No. 2015-013148, dated Dec. 4, 2015 (3 pgs).
Japanese Office Action issued in application No. 2016-005262, dated Jun. 30, 2016 (1 pg).
Japanese Office Action issued in application No. 2016-005263, dated Jun. 30, 2016 (1 pg).
Korean Design of Registration issued in Korean related Application Serial No. 30-2015-0029561, M001 (w/translation), dated Jun. 29, 2016 (3 pgs).
Korean Design of Registration issued in Korean related Application Serial No. 30-2015-0029561, M002 (w/translation), dated Jun. 27, 2016 (3 pgs).
Korean Office Action issued in application No. 30-2015-0029561, M002 (w/translation), dated May 23, 2016 (6 pgs).
Korean Office Action issued in application No. 30-2015-0029561, M001, dated May 23, 2016 (2 pgs).
Korean Office Action issued in application No. 30-2015-0029561, M002 (w/translation), dated Dec. 24, 2015 (7 pgs).
Korean Office Action issued in application No. 30-2015-0029561, M001 (w/translation), dated Dec. 24, 2015 (12 pgs).
Korean Office Action issued in application No. 30/2015-0029561, M001, dated Jun. 9, 2016 (16 pgs).
Korean Office Action issued in application No. 30-2015-0029561, M002, dated Jun. 9, 2016 (3 pgs).
Liang, Yafen et al., "Nasal Ventilation is More Effective than Combined Oral-Nasal Ventilation during Induction of General Anesthesia in Adult Subjects", Anesthesiology 2008, vol. 108, No. 6, Jun. 2008, pp. 998-1003.
Office Action issued in U.S. Appl. No. 29/530,124, dated Aug. 12, 2016 (17 pgs).
Office Action issued in related Design U.S. Appl. No. 29/520,420, dated Aug. 11, 2016 (18 pgs).
Sleep Medicine Solutions product description, http://sleepmedicinesolutions.net.au/cpap-spare-parts/26-fisher-paykel-zesy-foams.html, downloaded Jul. 28, 2016, 2 pages.
Sleepnet homepage, htips://web.arehive.org/web/20111031122613/http://www.sleepnetmasks.com/, downloaded Jul. 28, 2016, 4 pages.
U.S. Appl. No. 29/511,716, filed Dec. 12, 2014.
U.S. Appl. No. 29/520,420, filed Mar. 13, 2015.
U.S. Appl. No. 29/530,124, filed Jun. 12, 2015.
U.S. Appl. No. 14/901,647, filed Dec. 28, 2015.
U.S. Appl. No. 15/217,753, filed Jul. 22, 2016.
U.S. Appl. No. 15/127,758, filed Sep. 20, 2016.
U.S. Appl. No. 15/127,759, filed Sep. 20, 2016.
U.S. Appl. No. 15/127,760, filed Sep. 20, 2016.
U.S. Appl. No. 15/272,074, filed Sep. 21, 2016.
U.S. Appl. No. 15/272,160, filed Sep. 21, 2016.
U.S. Appl. No. 15/272,190, filed Sep. 21, 2016.
U.S. Appl. No. 29/520,420, filed Mar. 13, 2015, Reilly et al.
U.S. Appl. No. 29/530,124, filed Jun. 12, 2015, Reilly et al.

(56) References Cited

OTHER PUBLICATIONS

U.S. Appl. No. 14/901,647, filed Dec. 28, 2015, Pedro et al.
U.S. Appl. No. 15/217,753, filed Jul. 22, 2016, Pedro et al.
U.S. Appl. No. 15/127,758, filed Sep. 20, 2016, Pedro et al.
U.S. Appl. No. 15/127,759, filed Sep. 20, 2016, Pedro et al.
U.S. Appl. No. 15/127,760, filed Sep. 20, 2016, Pedro et al.
U.S. Appl. No. 15/272,074, filed Sep. 21, 2016, Pedro et al.
U.S. Appl. No. 15/272,160, filed Sep. 21, 2016, Pedro et al.
U.S. Appl. No. 15/272,190, filed Sep. 21, 2016, Pedro et al.
Preliminary Report on Patentability issued in application No. PCT/US2015/034277, dated Dec. 15, 2016 (11 pgs).
Notice of Decision of Registration for Design issued in Korean Design Application 30-20016-0014111, dated Dec. 13, 2016 (3 pages with translation).
Office Action Issued in U.S. Appl. No. 15/272,160, dated Jan. 4, 2017 (31 pgs).
Office Action Issued in U.S. Appl. No. 15/272,190, dated Jan. 30, 2017 (32 pgs).
Singapore Search Report issued in application 11201510589, dated Jan. 31, 2017 ( 1 pgs).
International Preliminary Report on Patentability issued in application No. PCT/US2015/044341, dated Mar. 2, 2017 (10 pgs).
Office Action issued in U.S. Appl. No. 29/520,420, dated Feb. 24, 2017 (14 pgs).
Office Action issued in U.S. Appl. No. 29/530,124, dated Feb. 28, 2017 (16 pgs).

\* cited by examiner

VENTILATION MASK

CROSS REFERENCE TO RELATED APPLICATION

This application claims priority from U.S. Provisional Application Ser. No. 62/394,405, filed Sep. 14, 2016.

BACKGROUND OF THE INVENTION

The present invention relates to improvements in anesthesia masks and ventilation masks.

During surgery a patient usually is placed under anesthesia. The most common delivery system consists of canisters containing anesthesia gases and oxygen, a system of regulating the gas flow and the patient's breathing, and a device ensuring the potency of the patient's airway for breathing, oxygenation and the delivery of the anesthetic gas mixture. A ventilation mask is used to provide oxygen to the patient either during emergency and/or elective airway management, which includes but is not limited to: before a patient is anesthetized for surgery while the patient is sedated during the surgery or procedure; while the patient is recovering from anesthesia; after the patient has recovered from anesthesia; and during any event where a patient requires supplemental oxygen. However, conventional ventilation masks are less then ideal.

Moreover, situations may arise during surgery that require rapid intubation of a patient. Full face masks, i.e. masks covering both the nose and mouth of a patient are problematic in emergency situations since a mask must be removed to uncover the mouth of a patient for intubation. However, removing the mask also removes oxygen support.

In our co-pending PCT Application Serial Nos. PCT/US2014/44934, PCT/US2015/034277 and PCT/US2015/044341 (hereinafter the '934, '277 and '341 PCT applications), we provide improved ventilation/anesthesia masks that overcome the aforesaid and other problems with the prior art by providing, in one aspect, a combination mask comprising a nasal portion or mask and an oral portion or mask defining respectively a nasal chamber and an oral chamber, detachably connected to one another wherein the nasal mask may be used separately or connected to the oral mask as a combination nasal/oral mask. We also provide a nasal mask with one or more ports, and various strap systems for holding the mask on a patient's face. We also provide a nasal only mask with one or more sensors for sensing end-tidal $CO_2$ or other gases, and for scavenging gases. See our co-pending PCT Application Serial No. PCT/US16/037070 (hereafter the '070 PCT application). Such combination nasal/oral masks and nasal only masks are available commercially from Revolutionary Medical Devices, Inc. of Tucson, Ariz., under the trademark SuperNO$_2$VA®.

SUMMARY OF THE INVENTION

The present invention provides improvements in nasal masks such as described in our aforesaid PCT applications, by providing an exhalation scoop adjacent the bottom of the nasal mask to overlay at least in part the upper lip of a patient, when the mask is worn. The exhalation scoop may be formed of a flexible, preferably resiliently deformable material, and fixed to the exterior of the mask by mechanical clips or the like, or an adhesive. Alternatively, the exhalation scoop may be formed with a lip to fit in a matching groove in the outer surface of the nasal mask, or formed integrally with the mask. The exhalation scoop is flexible so as to permit a surgeon to compress or push the exhalation scoop out of the way to permit access to the patient's mouth, while the nasal mask remains on the patient. Alternatively, the exhalation scoop may be folded back on itself leaving access to the patient's mouth, while the nasal mask remains on the patient.

In one aspect the invention provides a nasal mask having exhalation scoop formed of a the flexible or resiliently deformable material, fixed adjacent a lower portion of mask, adapted to overlie an upper lip of a patient when the mask is worn.

In another aspect the exhalation scoop is adapted to be pressed out of the way to permit access to the mouth of a patient.

In still another aspect the exhalation scoop is adapted to be folded back on itself to permit access to the mouth of a patient.

In yet another aspect, the mask includes an end-tidal $CO_2$ port for sampling exhaled $CO_2$ expelled from a mouth and/or nose of a patient.

In still yet another aspect the mask includes a ventilation port adapted to attach to an anesthesia machine, ventilation machine, hyperinflation bag or other ventilation or gas accessory.

In a still further aspect the mask further includes an oxygen port adapted for connection to an oxygen source for supplying oxygen to an interior of the mask.

In another aspect, the mask has tabs or eyelets for attaching one or more mask straps.

In yet another aspect the exhalation scoop is fixed to the mask or formed integrally with the mask.

The present invention also provides a method for ventilating a patient, comprising providing a nasal mask having exhalation scoop formed of a the flexible or resiliently deformable material, fixed adjacent a lower portion of mask, and adapted to overlie an upper lip of a patient when the mask is worn, and when needed, moving the exhalation scoop out of the way to provide access to the patient's mouth.

In one aspect of the method the exhalation scoop is pressed out of the way to permit access to the mouth of a patient.

In another aspect of the method the exhalation scoop is folded back on itself to permit access to the mouth of a patient.

In still yet another aspect the method includes providing a nasal mask with a exhalation scoop as described above, and monitoring end-tidal $CO_2$ port by sampling exhaled $CO_2$ expelled from a mouth and/or nose of a patient using an end-tidal $CO_2$ monitor.

In still yet another aspect, the mask is attached to an anesthesia machine, ventilation machine, hyperinflation bag or other ventilation or gas accessory, or to an oxygen source for supplying oxygen to an interior of the mask.

BRIEF DESCRIPTION OF THE DRAWINGS

Further features and advantages of the present invention will be seen from the following detailed description, taken in conjunction with the accompanying, wherein.

DETAILED DESCRIPTION OF THE INVENTION

Figure 1:
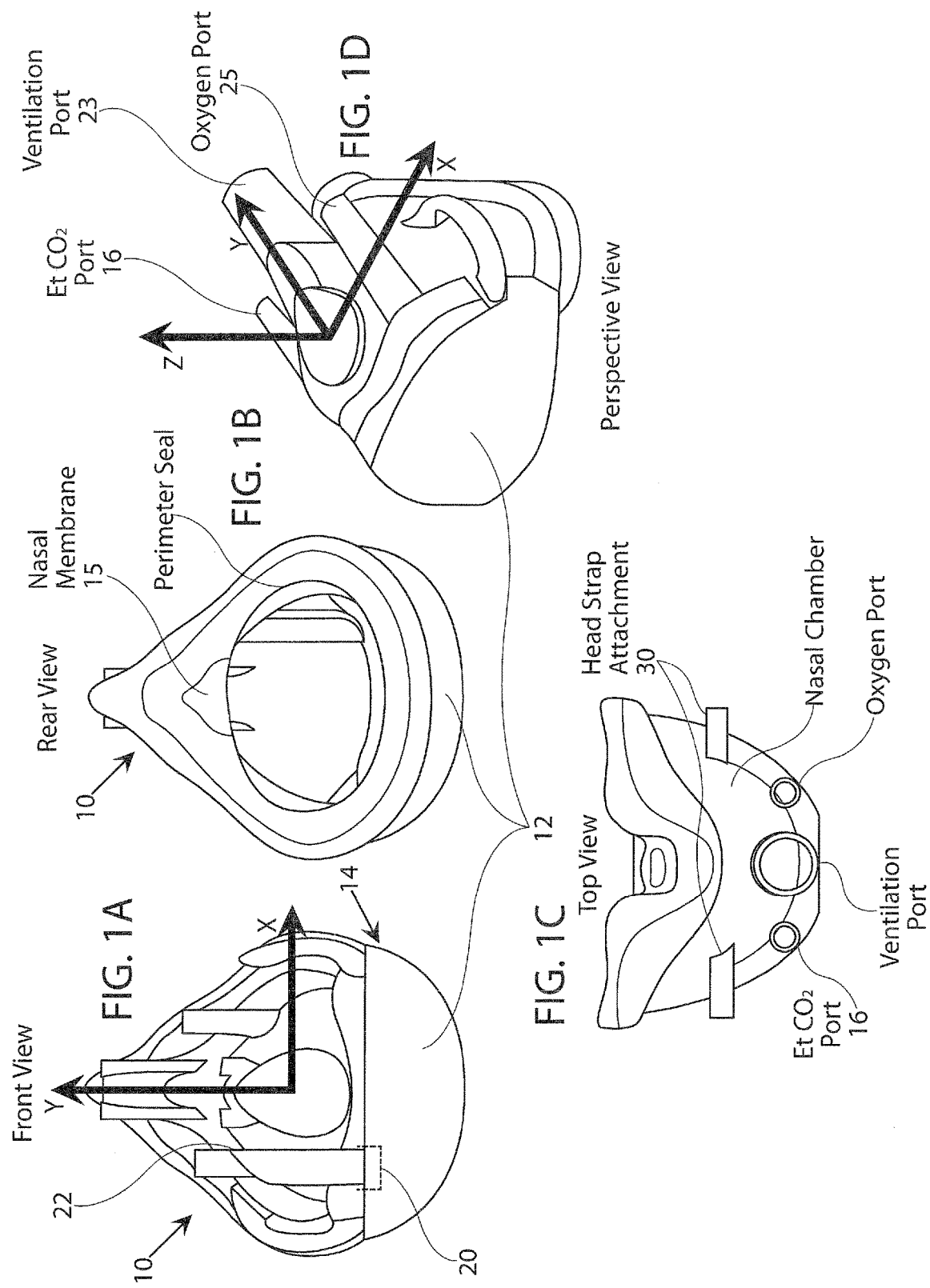
FIG. 1A-1D are front, rear, top and perspective views respectively, of a nasal mask incorporating an exhalation scoop in accordance with the present invention.

As used herein "nasal mask" preferably comprises a nasal mask similar to the nasal mask such as described in our aforesaid '934, '277, '341, and '070 PCT Applications including in particular a SuperNO$_2$VA® nasal mask available commercially from Revolutionary Medical Devices, Inc. of Tucson, Ariz.

FIGS. 1A-1D are front, rear, top and perspective views of a nasal mask 10 similar to the nasal mask described in our aforesaid PCT Application No. PCT/US16/37070, having a exhalation scoop 12 fixed to lower portion 14 of the mask. Exhalation scoop 12 is formed of a flexible, preferably resiliently deformable material. Exhalation scoop 12 may be formed of the same material forming the nasal membrane 15, and preferably has a Shore A Hardness durometer of 2-10, more preferably 3-7, most preferably 5.

Figure 2:
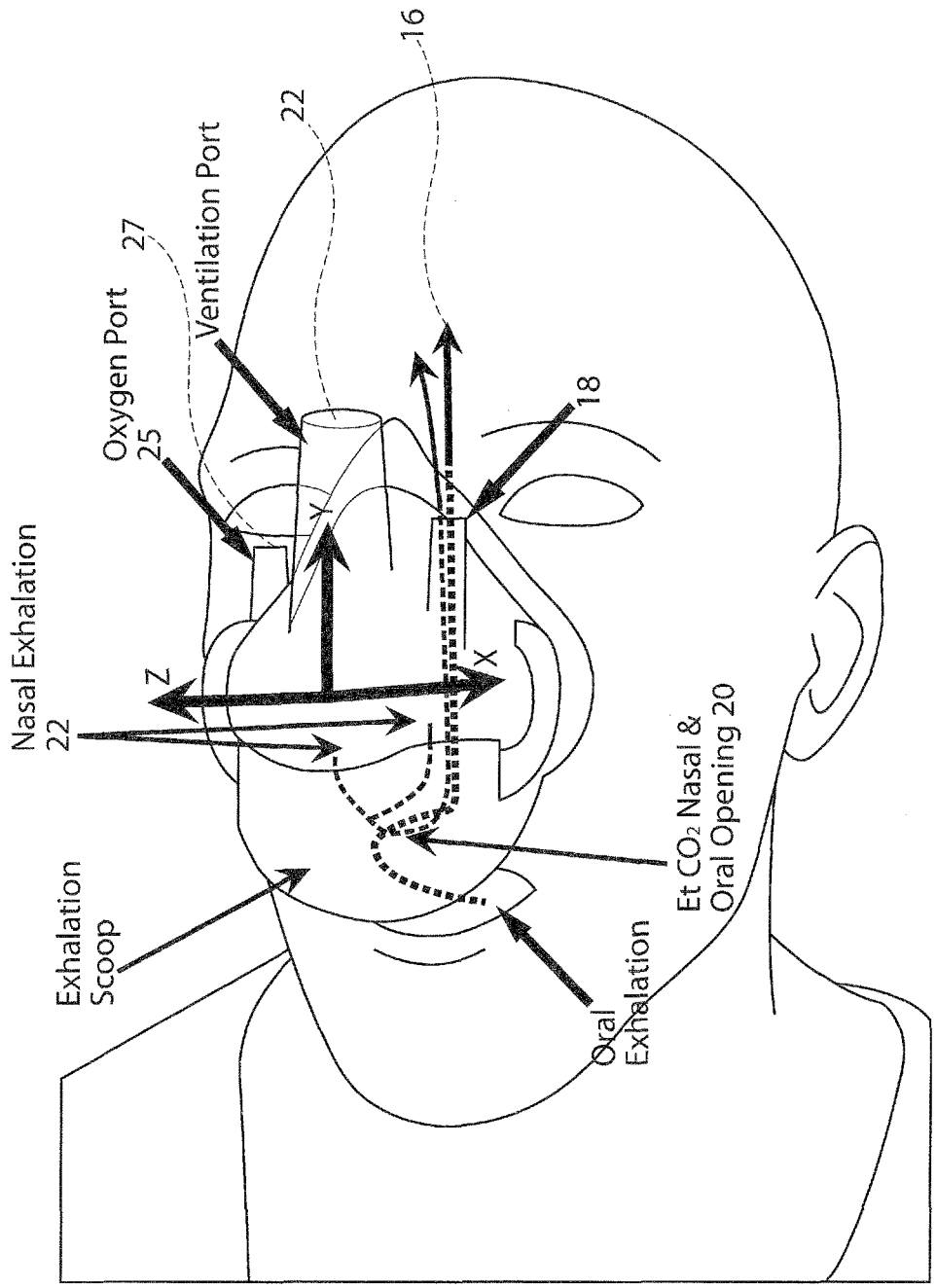
FIG. 2 is a perspective view showing nasal mask with an exhalation scoop in accordance with the present invention on a patient.

Referring also to FIG. 2, the mask 10 also includes a gas sampling device (shown in phantom at 16) has suction attached to an end-tidal ("ET") CO$_2$ port 18 and adapted for drawing gas samples from both the oral and nasal exhalations of the patient. One opening 20 of the EtCO$_2$ manifold is behind the exhalation scoop 12 to overlie the upper lip of a patient, when the mask is worn by a patient, on the exterior of the nasal mask 10, where a negative pressure (pressure less than atmospheric pressure) is created by a gas sampling device 16. A second opening 22 of the manifold is below the nares on the interior of the nasal mask where a negative pressure is also created by the gas sampling device 16. When the patient exhales, oral and nasal exhalation are collected through openings 20, 22 and proceed through the manifold and exit the EtCO$_2$ port that is connected to the gas sampling device 16 that provided the negative pressure. Concentration levels of the gas, such as CO$_2$ are then measured by gas sampling device 16.

The nasal mask interior chamber is pressurized through a ventilation port 23 by an anesthesia machine or another ventilation device (shown in phantom at 24). Flow from the patient's nose is drawn to the negative pressure of the opening of the manifold interior of the nasal chamber. The patient's mouth is at atmospheric pressure and the flow of the oral exhalation is channeled by the exhalation scoop where it is drawn by the negative pressure presented by gas sampling system through the manifold opening. Samples of both the nasal and oral exhalation flow through a manifold, and exit the EtCO$_2$ port 18 to the gas sampling device 16. The mask 10 also includes an oxygen port 25 for supplying oxygen from an oxygen source (shown in phantom at 27) to a patient.

Figure 3:
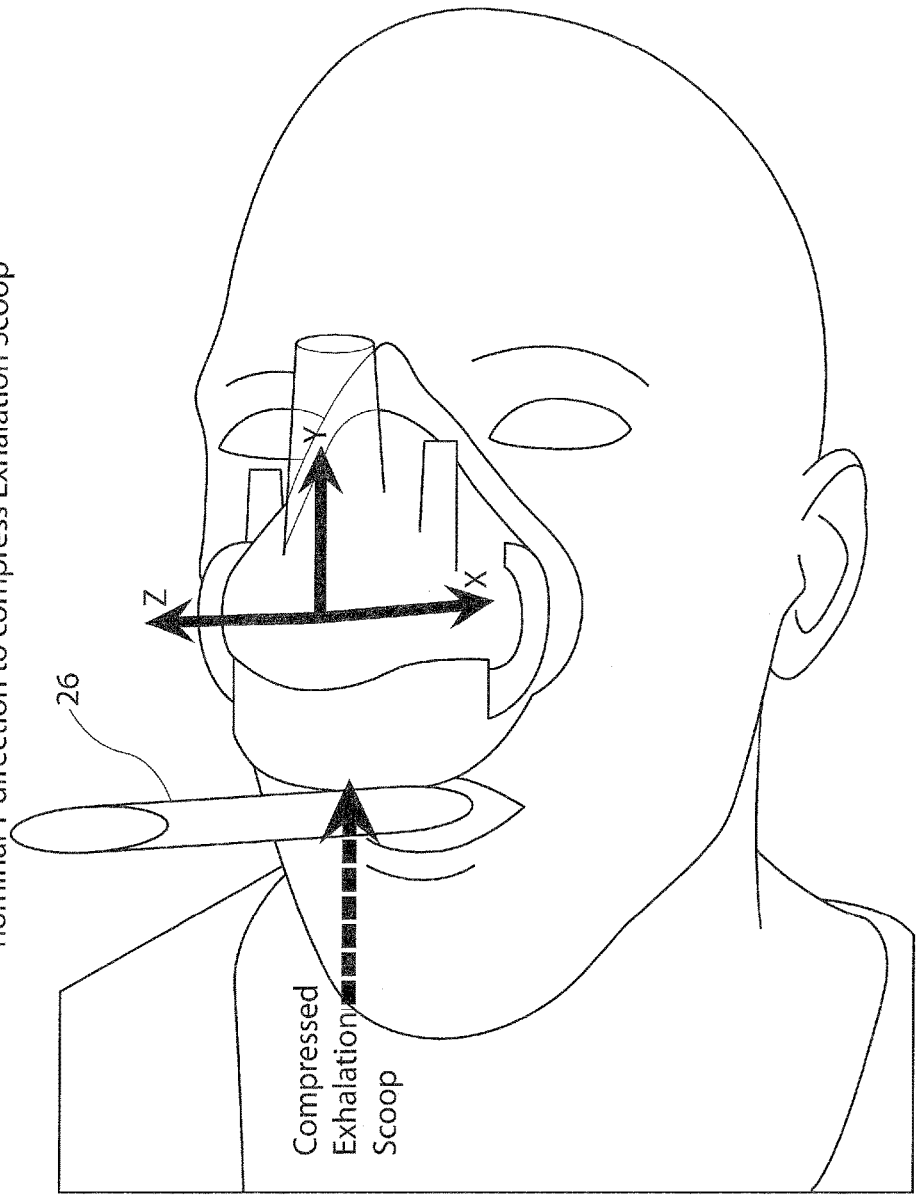
FIG. 3 is a view similar to FIG. 2, showing the exhalation scoop compressed or pushed out of the way to provide oral access.

One benefit of the flexible exhalation scoop design is that if the surgeon requires access to the patients mouth to employ a device such as an intubation tube or endoscope 26, the exhalation scoop 12 can be flexed or pushed by the device in the nominal "y" direction, providing access to the patient's mouth as shown in FIG. 3.

Figure 4:
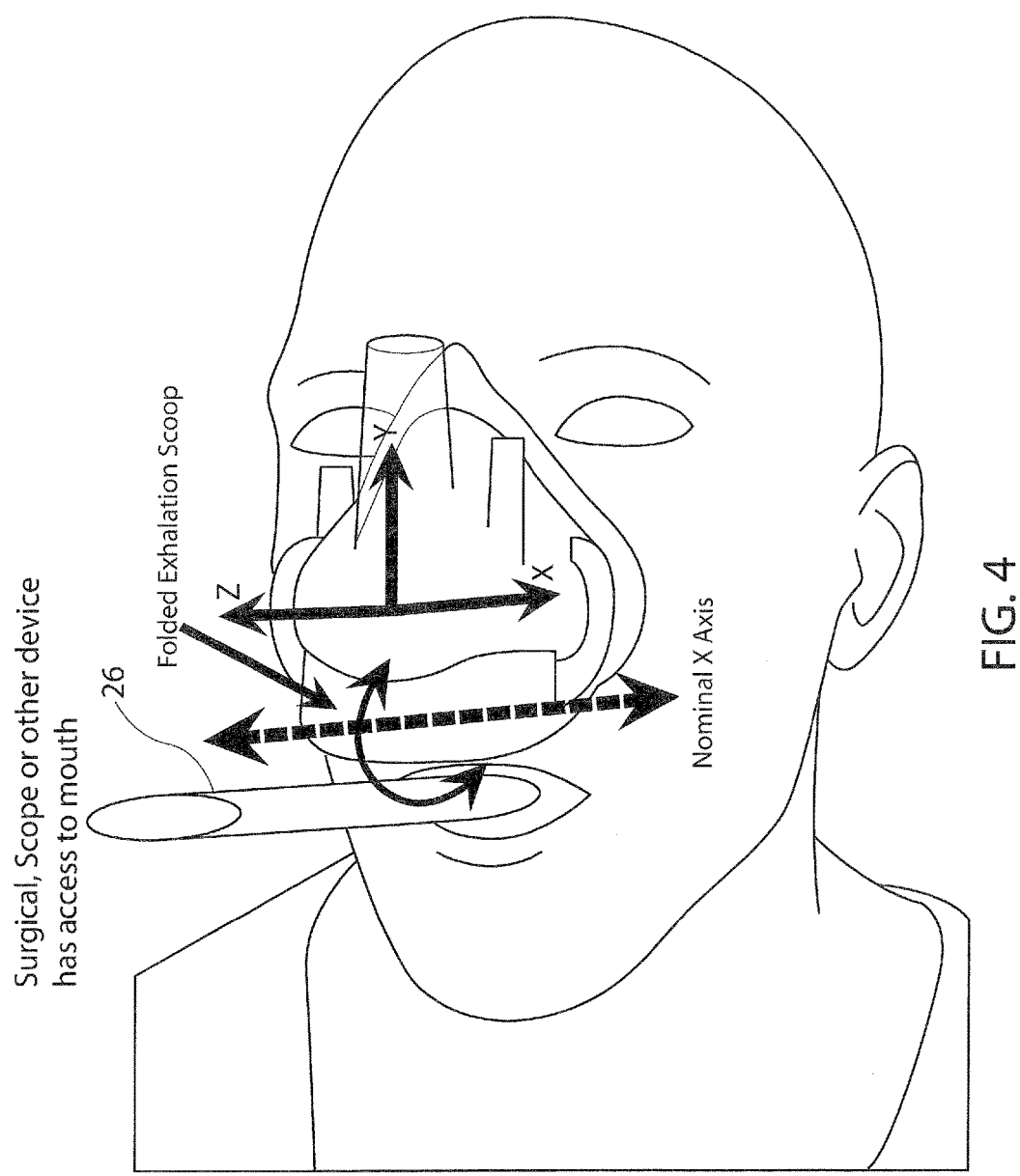
FIG. 4 is a view similar to FIG. 2, showing a nasal mask with an exhalation scoop folded out of the way to provide oral access.

Another benefit of one flexible exhalation scoop 12 design is that if the surgeon requires access to the patient's mouth, that there exists a bi-stable condition where the scoop 12 overlies the upper lip and/or mouth of the patient, as shown in FIG. 2, or the scoop 12 can be folded over itself about the nominal—"X" axis and remain stable with the scoop 12 no longer covering the mouth as shown in FIG. 4. This allows access to the patient's mouth as shown, and nasal Et CO$_2$ can still be collected. Once the endoscope 26 or other device is removed from the patient's mouth, should the clinician decide to continue collecting oral Et CO$_2$ samples, the flexible exhalation scoop 12 can be unfolded about the "X" axis, again covering the patient's mouth as in FIG. 2.

Completing the nasal mask are tabs\or eyelets 30 for attaching one or more head straps (not shown).

What is claimed:

1. A method for ventilating a patient, comprising
providing a nasal mask having an exhalation scoop formed of a flexible or resiliently deformable material, fixed adjacent a lower portion of the mask, and adapted to overlie an upper lip of the patient when the mask is worn, and when needed, folding the exhalation scoop back on itself to provide access to the patient's mouth.

2. The method of claim 1, further including monitoring end-tidal CO$_2$ by sampling exhaled CO$_2$ expelled from the mouth and/or nose of the patient via an end-tidal CO$_2$ port.

3. The method of claim 1, further including attaching the mask to an anesthesia machine, ventilation machine, hyperinvation bag or a ventilation or gas accessory.

4. The method of claim 1, further including attaching the mask to an oxygen source for supplying oxygen to an interior of the mask.

5. The method of claim 1, wherein the exhalation scoop is formed of a flexible or resiliently deformable material having a Shore A Hardness durometer selected from 2-10.

6. The method of claim 1, wherein the exhalation scoop is formed of a flexible or resiliently deformable material having a Shore A Hardness durometer of about 5.

7. The method of claim 1, wherein the exhalation scoop is formed of a flexible or resiliently deformable material having a Shore A Hardness durometer of 3-7.

* * * * *